United States Patent
Vinterback et al.

(10) Patent No.: US 11,536,657 B2
(45) Date of Patent: Dec. 27, 2022

(54) SENSOR SURFACE FOR SURFACE PLASMON RESONANCE ASSAYS

(71) Applicant: GE Healthcare Bio-Sciences AB, Uppsala (SE)

(72) Inventors: Lena Vinterback, Uppsala (SE); Anna Lager, Uppsala (SE); Per Kjellin, Uppsala (SE); Tomas Dalmo, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 225 days.

(21) Appl. No.: 16/620,908

(22) PCT Filed: Jun. 7, 2018

(86) PCT No.: PCT/EP2018/064964
§ 371 (c)(1),
(2) Date: Dec. 10, 2019

(87) PCT Pub. No.: WO2018/228903
PCT Pub. Date: Dec. 20, 2018

(65) Prior Publication Data
US 2020/0191715 A1 Jun. 18, 2020

(30) Foreign Application Priority Data
Jun. 15, 2017 (GB) .................................. 1709503

(51) Int. Cl.
*G01N 21/552* (2014.01)
*G01N 33/543* (2006.01)
*G01N 33/557* (2006.01)

(52) U.S. Cl.
CPC ..... *G01N 21/554* (2013.01); *G01N 33/54373* (2013.01); *G01N 33/557* (2013.01); *G01N 2610/00* (2013.01)

(58) Field of Classification Search
CPC .......... G01N 21/554; G01N 33/54373; G01N 33/557; G01N 2610/00; G01N 33/54393
See application file for complete search history.

(56) References Cited

U.S. PATENT DOCUMENTS 5,242,828 A * 9/1993 Bergstrom ............. C12Q 1/002
422/425
6,127,129 A * 10/2000 Corn ...................... B82Y 30/00
435/6.19

(Continued)

FOREIGN PATENT DOCUMENTS

DE 10210058 A1 9/2003
EP 1790984 A2 5/2007

(Continued)

OTHER PUBLICATIONS

Translation of DE10210058A1, Hans-Heinrich, Trutnau, Sep. 18, 2003 (Year: 2003).*

(Continued)

*Primary Examiner* — Samuel P Siefke
*Assistant Examiner* — Henry H Nguyen
(74) *Attorney, Agent, or Firm* — Eversheds Sutherland (US) LLP

(57) ABSTRACT

The present invention relates to a method for production of an improved sensor surface for an SPR instrument, comprising forming a self assembled monolayer (SAM) on a surface and attaching ligands and protein resistant groups, preferably polyethylene glycol (PEG), directly to functional groups on said surface. The invention also relates to a sensor surface produced by these methods use thereof in SPR (surface plasmon resonance) assays or interactions.

13 Claims, 3 Drawing Sheets

1. Gold chip (Sensor surface coated with a thin layer of gold)
2. 16-Mercaptohexadecanoic acid (MHA) is added
3. SAM of MHA on gold chip
4. EDC/NHS - activation of carboxyle on MHA
5. Amine-PEG*- (5 kD) is covalently coupled on the MHA-SAM layer
6. Deactivation with Ethanolamine

*Polyethylene glycol

(56) References Cited

U.S. PATENT DOCUMENTS

| | | | |
|---|---|---|---|
| 2003/0017579 A1 | 1/2003 | Corn et al. | |
| 2008/0038841 A1 | 2/2008 | Ezoe et al. | |
| 2010/0151491 A1* | 6/2010 | Himmelhaus | A61L 27/54 |
| | | | 435/7.2 |
| 2016/0299135 A1 | 10/2016 | Cameron et al. | |

FOREIGN PATENT DOCUMENTS

| | | | | |
|---|---|---|---|---|
| JP | 2002543429 A | 12/2002 | | |
| JP | 2003514224 A | 4/2003 | | |
| JP | 2004125625 A | 4/2004 | | |
| JP | 2004150828 A | 5/2004 | | |
| JP | 2005140576 A | 6/2005 | | |
| JP | 2009216483 A | 9/2009 | | |
| WO | 2001035081 A1 | 5/2001 | | |
| WO | WO-0135081 A1 * | 5/2001 | | C12Q 1/6825 |

OTHER PUBLICATIONS

PCT International Search Report and Written Opinion for PCT Application No. PCT/EP2018/064964 dated Aug. 20, 2018 (11 pages).

Great Britain Search Report for GB Application No. 1709503.5 dated Mar. 12, 2018 (8 pages).

Fernandez et al., "A Label-Frfee and Portable Multichannel Surface Plasmon Resonance Immunosensor for on Site Analysis of Antibiotics in Milk Samples," Biosensors and Bioelectronics, 2010, 26:1231-1238.

Frederix et al., "Enhanced Performance of an Affinity Biosensor Interface Based on Mixed Self-Assembled Monolayers on Thiols on Gold," Langmuir, 2003, 19:4351-4357.

Islam et al., "Effects of Composition of Oligo-ethylene glycol)-Based Mixed Monolayers on Peptide Grafting and Human Immunoglobulin Detection," J. Phys. Chem. C, 2014, 118:5361-5373.

Ladd et al., "DNA-Directed Protein Immobilization on Mixed Self-Assembled Monolayers via a Steptavidin Bridge," Langmuir, 2014, 20:8090-8095.

Raghupathi, "Strategies for Creating Antifouling Surfaces Using Self-Assembled Poly(ethylene glycol) Thiol Molecules," 2011, http://pure.au.dk/ws/f/40363364/Arcot_Thesis_iNANO_School.

Yoshioka et al., "One-Step Detection of Galectins on Hybrid Monolayer Surface with Protruding Lactoside," Anal. Chem., 2010, 82:1175-1178.

JP2019-569393 Office Action dated May 9, 2022, 3 pages, in the Chinese Language; Summary of JP Office Action in English Lanuage, 3 pages.

* cited by examiner

1. Gold chip (Sensor surface coated with a thin layer of gold)
2. 16-Mercaptohexadecanoic acid (MHA) is added
3. SAM of MHA on gold chip
4. EDC/NHS – activation of carboxyle on MHA
5. Amine-PEG*- (5 kD) is covalently coupled on the MHA-SAM layer
6. Deactivation with Ethanolamine

*Polyethylene glycol

Ligand is immobilized to carboxyles on the MHA self assembled monolayer.

The polyethylene glycol matrix is not involved in the ligand immobilization.

| Kinetics model | ka (1/Ms) | kd (1/s) | KD (M) |
|---|---|---|---|
| 1:1 binding | 2,20E+06 | 2,19E-03 | 9,95E-10 |

SENSOR SURFACE FOR SURFACE PLASMON RESONANCE ASSAYS

CROSS REFERENCE TO RELATED APPLICATIONS

This application claims the priority benefit of PCT/EP2018/064964 filed on Jun. 7, 2018, which claims priority benefit of Great Britain Patent Application No. 1709503.5 filed on Jun. 15, 2017, the entire contents of which are hereby incorporated by reference herein.

FIELD OF THE INVENTION

The present invention relates to a method and device for assay improvement. More closely the invention relates to production of an improved sensor surface and use thereof in SPR (surface plasmon resonance) assays or interactions. The invention also relates to a sensor surface produced by these methods.

BACKGROUND OF THE INVENTION

Analytical sensor systems that can monitor interactions between molecules, such as biomolecules, in real time are gaining increasing interest. These systems are often based on optical biosensors and usually referred to as interaction analysis sensors or biospecific instrumentation, which uses surface plasmon resonance (SPR) for detecting interactions between molecules in a sample and molecular structures immobilized on a sensing surface. As sample is passed over the sensor surface, the progress of binding directly reflects the rate at which the interaction occurs. Injection of sample is followed by a buffer flow during which the detector response reflects the rate of dissociation of the complex on the surface. A typical output from the BIACORE® system from GE Healthcare is a graph or curve describing the progress of the molecular interaction with time, including an association phase part and a dissociation phase part.

With the BIACORE® system (and analogous sensor systems) it is thus possible to determine in real time without the use of labelling, and often without purification of the substances involved, not only the presence and concentration of a particular molecule (analyte) in a sample, but also additional interaction parameters, including kinetic rate constants for binding (association and dissociation) in the molecular interaction as well as the affinity for the surface interaction. The association rate constant ($k_a$) and the dissociation rate constant ($k_d$) can be obtained by fitting the resulting kinetic data for a number of different sample analyte concentrations to mathematical descriptions of interaction models in the form of differential equations. The affinity (expressed as the affinity constant $K_A$ or the dissociation constant $K_D$) can be calculated from the association and dissociation rate constants.

When molecules in the sample bind to the capturing molecules on the sensor chip surface, the concentration, and therefore the refractive index at the surface changes and an SPR response is detected. Plotting the response against time during the course of an interaction will provide a quantitative measure of the progress of the interaction. Such a plot, or kinetic or curve (binding isotherm), is usually called binding curve or sensorgram, also sometimes referred to in the art as "affinity trace" or "affinogram". In the BIACORE® system, the SPR response values are expressed in resonance units (RU). One RU represents a change of 0.0001° in the angle of minimum reflected light intensity, which for most proteins and other biomolecules correspond to a change in concentration of about 1 pg/mm$^2$ on the sensor surface. As sample containing an analyte contacts the sensor surface, the capturing molecule (ligand) bound to the sensor surface interacts with the analyte in a step referred to as "association." This step is indicated in the binding curve by an increase in RU as the sample is initially brought into contact with the sensor surface. Conversely, "dissociation" normally occurs when the sample flow is replaced by, for example, a buffer flow. This step is indicated in the binding curve by a drop in RU over time as analyte dissociates from the surface-bound ligand.

Thus, a vital part of an SPR instrument system is the sensor surface, where the interactions to be studied take place. It may consist of a glass surface coated with a thin layer of gold, on top of which a hydrophilic layer, called the matrix, is created on top of a self-assembled monolayer (SAM) that prevents non specific binding (NSB) to the gold chip. The sensor surface may also be a rigid substrate having a surface layer of different materials, such as the polymers (poly)tertrafluoroethylene, (poly)vinylidene difluoride, or combinations thereof.

A commonly used matrix is the carboxymethylated dextran (CMDx), a flexible carbohydrate polymer with low non-specific binding properties that forms a three-dimensional structure on the sensor surface. As the technical development advances, with a rising sensitivity of the SPR instrumentation hardware, demands on the sensor surface chemistry are increased. It becomes particularly important to minimize drift and non-specific binding of biomolecules to be able to detect low interaction signals. Ligands are immobilized on the dextran matrix through the carboxyl groups. Most of the carboxyl groups are not involved in ligand immobilization, they are hydrolyzed to carboxyl groups after activation or not activated.

The matrix characteristics are dependent on the buffer condition used, for example different pH and salt concentration result in differences in matrix expansion in relation to surface due to different degree of negative charges and charge repulsion. Differences in buffer conditions due to samples and buffer differences in samples and the buffer flow etc during an assay leads to differences in dextran expansion, this causes baseline drift. This matrix changes have impact on the SPR signal (baseline drifts) and negative impact on assay performance. The matrix expansions should be minimized in assays. With ligand immobilized on matrix there is a high risk that matrix movements cause larger signal changes and negative impact on assay (analysis) performance.

Different capturing molecules/ligands show different properties to other buffer components. A common component in assay buffer is detergent. Detergent properties depend on type of assay. Different detergents bind different to different types of matrices.

Different targets and samples have different requirement on the sensor surface. CMDx is useful for many different types of samples and assay but there is a need for alternative matrices when dextran doesn't work. Therefore, there is a need of improved sensor surfaces minimizing drift and non-specific binding.

It is general known that a PEG (polyethylene glycol) or OEG (oligoethylene glycol) surface has protein repellant properties, and PEG or OEG has been used on sensor surfaces to decrease unwanted binding in assay. In such technologies, the PEG or OEG moieties are also used for attachment of one of the interactants (capturing molecules), to be included in the interaction analysis. Alternatively the ligands and protein resistant compounds are coupled to separate fractions of the hydrogel, such as CMDx, as described in WO2006/041392. However, the surfaces may not be suitable for some sensitive samples since they suffer from base line fluctuations.

There are also examples of sensor chip with OEG surfaces, constructed through alkane-OEG SAM layer wherein ligand is immobilized to OEG. One example is a planar polyethylene glycol carboxyl sensor chip sold by Reicherts (reichertspr.com).

However, dependent on type of sample several of the currently known matrices suffer from several drawbacks, such as high background noise and non-specific binding. There is therefore a need for sensor surfaces with alternative matrices and polymers.

SUMMARY OF THE INVENTION

The present inventors have found that assay noise can be reduced by minimizing matrix fluctuations on a SPR sensor surface by a combination of immobilization of an inert matrix and of capturing molecule(s) to the SAM.

In a first aspect, the invention provides a method for production of a sensor surface for an SPR instrument, comprising forming a self-assembled monolayer (SAM) on a surface by reacting said surface with one or more thiol $C_{10}$-$C_{30}$ alkane reagent(s), having at least one functional group, wherein one or more protein resistant compound(s) is/are coupled to a first fraction of the functional groups; and wherein one or more capturing molecule(s) is/are directly coupled to a second fraction of the functional groups or via a linker which is not said protein resistant compound, wherein no capturing molecule is coupled to the protein resistant compound. Functional groups for ligand immobilization are only available on the SAM and not on the protein resistant compounds/matrix.

The surface is a metal, preferably gold or silver, plated surface or any other surface suitable for SPR applications.

The second fraction of the functional groups are comprised among those remaining on the surface after coupling the protein resistant compound via the first fraction of the functional groups.

The functional groups on SAM are used for coupling of capturing molecules and protein resistant compound. The same or different types of functional groups may be used for these couplings and the same or different linkers, if present, may be used.

The protein resistant compound(s) are also called matrix forming compound or just matrix and may be coupled via a linker to the surface. The capturing molecule is either one of the interactants, ie the ligand directly interacting with the analyte, or may bind the ligand, as in conventional formats in the art. The invention is not limited to the type of binding reaction but relates to any type of reaction between an analyte and its binding partner.

The linker may for example be epichlorohydrin, cystamine, bi-functional activation reagents, carbohydrazide, etc.

The functional group of the $C_{10}$-$C_{30}$ thiol alkane reagent is preferably one or more of a carboxyl, a hydroxyl, an amino, an aldehyde, an epoxy, a vinyl, a carbonyl or thiol group. Or a pre-activated group ready for immobilization of ligand. The protein resistant group may be immobilized to the same or different functional group on SAM as the capturing molecule.

Preferably the $C_{10}$-$C_{30}$ thiol alkane reagent is MHA (mercapto hexadecanoic acid) or derivatives thereof.

In a preferred embodiment of the invention the protein resistant compound is a hydrophilic polymer selected from polyethylene glycol or derivatives thereof, e.g. methoxy poly ethylene glycol amine, having a weight average molecular weight (mw) <20000. Most preferably the protein resistant compound is PEG with an mw of 100-20000, preferably mw 2000-10000, most preferably mw 4000-6000.

In one embodiment of the method according to the invention the second fraction of the functional groups may be activated before coupling of the capturing molecule or ligand and the amount of coupled capturing molecule (ligand) is inversely proportional to the length of activation time which is over about 5 sec.

A method for running an SPR assay using a sensor surface produced according to the invention comprises addition of an analyte possibly interacting with the capturing molecule (ligand) on the sensor surface and performing a kinetic assay and/or concentration assay.

In a second aspect, the invention relates to a sensor surface, comprising a substrate or chip of the type commonly used for SPR, such as a metal plated surface, with a self assembled monolayer (SAM) provided with functional groups directly on said SAM, wherein a protein resistant compound is coupled to a first fraction of the functional groups and wherein a capturing molecule (ligand) is coupled to a second fraction of the functional groups on the surface, but no ligand is coupled to the protein resistant compound.

Preferably the surface is a metal plated, preferably gold plated, surface and the SAM is a thiol-alkane $C_{10}$-$C_{30}$ SAM, most preferably MHA-SAM, and the protein resistant compound is polyethylene glycol (PEG) or derivatives thereof. In a preferred embodiment the protein resistant compound is PEG mw 5000 in a concentration of 0.05-50 mM, preferably 0.5-5 mM.

DETAILED DESCRIPTION OF THE INVENTION

Figure 1:
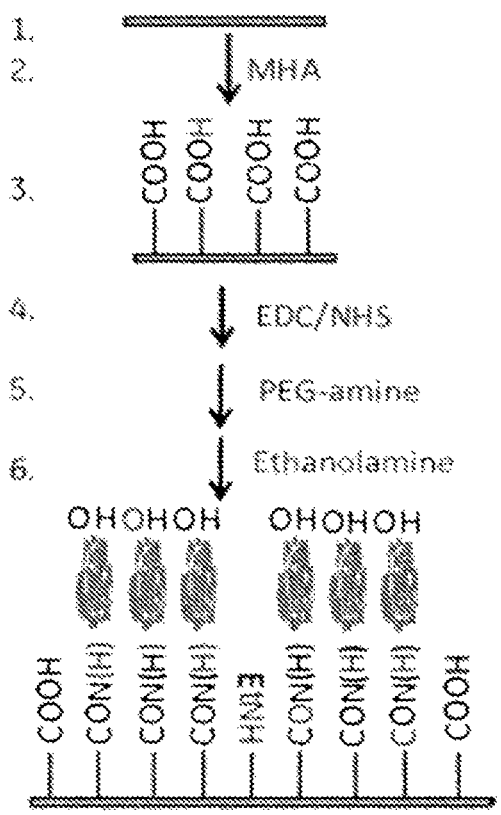
FIG. 1 is a schematic view of the method steps in the production of a sensor surface of the invention.
Figure 2A:
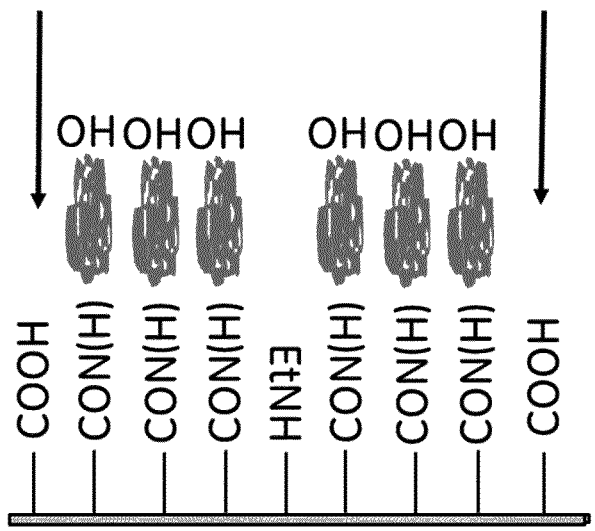
FIG. 2A is a schematic view with arrows to the functional groups where specific ligands are attached to the sensor surface in FIG. 1.
Figure 2B:
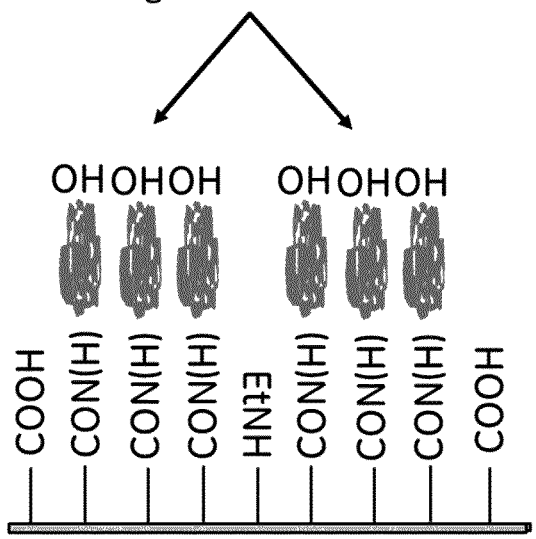
FIG. 2B shows that the PEG groups are not involved in ligand immobilization.

In a pre-study the inventors have found that self-assembled monolayers (SAMs) created from oligo(ethylene glycol) (OEG) derivatized alkanethiol compounds, or a mixture of these compounds with alkanethiol compounds without OEG, showed high non-specific binding. Poor result from cyclic voltametric analysis indicated unfavourable packing density and poor surface coverage and therefore high probability of non-wanted and non-specific binding to gold surface/disrupted SAM from samples. This result indicates that surfaces with SAM alkanethiol-OEG are unsuitable for high sensitivity applications.

The present invention provides a novel sensor surface wherein the capturing molecule will be bound closely to the sensor surface and not bound to any matrix molecule to minimize baseline drifts. The capturing molecule is bound directly to an alkanethiol SAM layer (or through linker on SAM), not via PEG or OEG or any other hydrophilic or protein resistant part. The invention provides a method comprising creating a sensor surface with alkane-SAM to achieve isolating properties, wherein in a second step a hydrophilic matrix is introduced to achieve protein repellant properties while providing available functional groups for ligand immobilization on the SAM to achieve low baseline drifts.

With thiol-alkanes, such as $C_{10}$-$C_{30}$ alkanes, reagents self-assembled monolayers (SAMs) can be created on gold surfaces. SAM $C_{16}$ show high density SAM with good isolating properties which is needed to avoid non-specific binding from sample components to the gold surface and any disrupted SAM component on the sensor surface.

A protein resistant compound forming matrix, such as a PEG matrix, is covalently immobilized through functional groups on the SAM layer. The matrix molecule is added solely for its protein repellant properties or other properties beneficial for the assay. Thus, both the ligand and protein resistant compound (matrix) are coupled directly to the SAM monolayer or via a linker. The linker may for example be epichlorohydrine The linker is a short molecule and not to a hydrophilic compound as in prior art.

An advantage of the invention is that there is no ligand immobilization to the protein resistant compound (matrix). If identical ligands were to be immobilized on the matrix and SAM then the immobilized ligands would represent two different ligand populations, one population immobilized on the SAM layer and one population immobilized on the matrix. This would impact the assay results negatively. With the invention, all ligands are immobilized only on SAM functional groups since the PEG matrix or alternative matrices or mixture of matrices are immobilized in a separate step on SAM functional groups and do not have functional groups to be used for ligand immobilization. After deactivation (optional) remaining functional groups on the SAM monolayer are available for ligand immobilization.

In the present invention, a preferred thiol-alkane reagent is MHA 16 (mercapto hexadecanoic acid). If the thiol-alkane reagent is MHA, a PEG molecule with a primary amine can be covalently attached to the carboxy moiety on the MHA SAM layer on the sensor surface. The PEG molecule with primary amine group can be covalently attached to a SAM layer with COOH (carboxy groups) through EDC/NHS chemistry. Sensor surfaces with amine functionalized PEG-molecules (such as 5 kDa) coupled to a carboxylated alkanethiol SAM show good matrix stability characteristics and proved to have high resistance towards non-specific binding from plasma samples and detergents.

Protein resistant compounds (matrix) and ligands can also be immobilized through other functional groups on the SAM layer. Example of possible functional groups on the SAM layer for immobilization are: hydroxyl, amino; carboxyl, aldehyde, carbonyl, epoxy, vinyl and thiol.

Example of possible functional group on the protein resistant compound (matrix) to be involved in immobilization on the SAM layer are: hydroxyl, amino; carboxyl, aldehyde, carbonyl, epoxy, vinyl and thiol. After immobilization of the protein resistant compound (matrix) to the SAM layer, any remaining functional groups on the protein resistant compound (matrix) must not be available, that is not used for ligand/capture immobilization, and/or de-activated if needed. Alternatively, they can be different from the functional group on SAM to be used for ligand immobilization.

Immobilization of protein resistant compound (matrix) to the SAM layer occurs through spontaneous covalent coupling or through activation of functional groups on either the matrix or on the SAM layer, for example aldehyde on the SAM and hydrazine on the matrix. Deactivation is performed of non-reacted activated or reactive groups. Stabilization of matrix or linker might be included, for example the coupling between aldehyde and hydrazine is stabilized by $NaCNBH_4$.

Activation and de-activation procedures are known for a skilled person in the art and may be for example activation of SAM or matrix by introducing an active ester through EDC/NHS chemistry or introducing epoxide through epichlorhydrine. Alternatively, activation with established chemistry through bi-functional reagents, for example amine groups on the surface and NHS derivative on the bifunctional reagents and reactive disulphide from bi-functional reagents for ligand immobilization.

Ligand Immobilization

There are a number of different coupling chemistries to enable ligand immobilization to COOH groups on sensor surfaces (chip surface). The most common route is to use amine coupling, whereby carboxyl groups on the chip surface are used for covalent amide bonds with primary amine groups in proteins (ligands). However, this process does not occur spontaneously, the carboxyl groups need to be activated. Activation is performed with a mixture of N-Ethyl-N'-(3-Dimethylaminopropyl) Carbodiimide (EDC) and N-Hydroxy-succinimide (NHS). EDC reacts with the carboxyl group and forms a reactive intermediate which in turn reacts with NHS to form an active NHS ester. As ligand is passed over the sensor chip surface, the NHS-moiety (which is a good leaving group) reacts spontaneously with a primary amine group on the ligand and covalent bond between ligand and chip surface is formed. Most proteins contain several primary amines, and thus, immobilization can be achieved without seriously affecting the ligand's biological activity.

To facilitate ligand immobilization, attractive electrostatic forces are employed in a process called pre-concentration. The ligand is dissolved in a coupling buffer with pH below the isoelectric point (pI) of the protein, but above the pI of the chip surface.

Hereby, the ligand and chip surface obtain opposite net charges. Positively charged ligand molecules are electrostatically attracted to the negative surface and a high ligand concentration near the surface results in more efficient immobilization After ligand immobilization, excess NHS-activated carboxyl groups are deactivated with for example ethanolamine or NaOH that removes residual NHS esters so that no more protein can be immobilized to the surface during analyte injection. The process may also be performed with a positively charged surface and negatively charged ligands.

The ligand level can be controlled through variation of ligand concentration, contact time for activation or ligand, composition and pH for ligand immobilization/coupling buffer or combination of this parameters. The present inventors have surprisingly found that with sensor surfaces with a MHA SAM layer according to the present invention, the ligand level is often increased with decreased activation time. This is inversed compared to available sensor surfaces with hydrogels such as CMDx. For the latter ligand level is increased with increased activation time (contact time).

Experimental Section

Experiment 1: Synthesis of Sensor Surface with MHA SAM and PEG

For this Example reference is made to FIG. 1.

Substrates comprising glass chips with gold surface were immersed in 80%/20% Ethanol/water with 1 mM MHA at 25° C. and incubated over-night. The gold chips were washed with following solutions for 5 minutes and in mentioned order; 100% Ethanol, 80% Ethanol, 50% Ethanol, 20% Ethanol and 100% water.

The sensor chips were dried with nitrogen gas and immersed 0.144 M EDC and 0.050 M NHS in water and incubated for 30 minutes at 25° C. The sensor chips were washed 4 times with water and thereafter immersed in 0.252 M sodium phosphate buffer pH 8.5 with 1.79 mM O-(2-aminoethyl) polyethylene glycol mw 5000 and incubated for 30 minutes at 25° C. The PEG solution was discarded and remaining active esters were deactivated with 1 M Ethanolamine pH 8.5. Finally the sensor chips were washed four times with water. The chips were dried with nitrogen gas.

Experiment 2: Immobilization of Ligand (Antibody) to Carboxyl Groups on SAM MHA Using Different Activation Times The chip from Experiment 1 was assembled with plastic carrier and hood. Thereafter, the chip was docked in Biacore 3000 according to the manufacturer's instruction in control software. The carboxyl groups on the SAM were activated in the instrument with a mixture of 200 mM EDC and 50 mM NHS in water for 30, 60, 90 and 180 seconds.

50 µg/ml Mouse IgG1 antibody in 10 mM sodium acetate pH 5 was injected over the activated chip surface for 7 minutes. The chip surface (not reacted succinimide esters) was deactivated with 1 M Ethanolamine pH 8.5 for 5 minutes. Immobilization with different activation times were performed in different flow cells. Running buffer HBS-EP (BR100188) (GE Healthcare).

Figure 3:
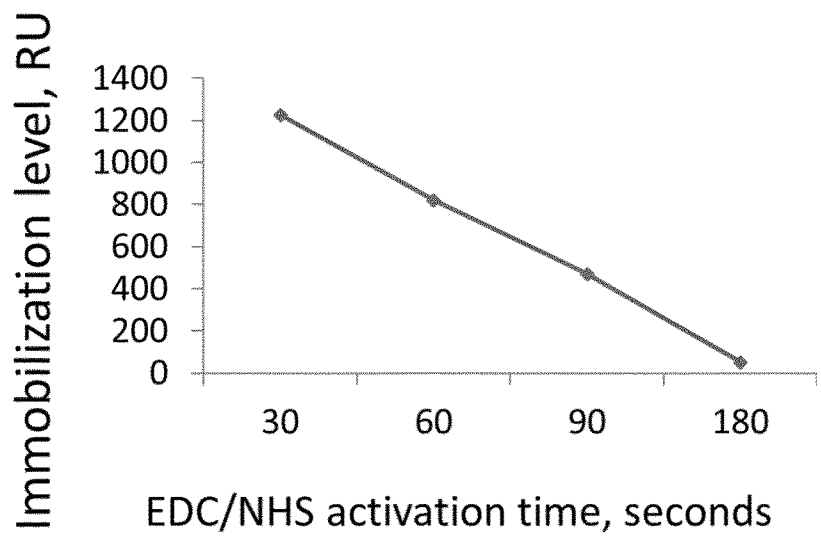
FIG. 3 is a graph showing the results of activation time vs ligand level starting with a sensor surface of the invention.

For this Example reference is made to the graph in FIG. 3 which shows that the immobilization level is inversely proportional against the activation time after 30 seconds.

Experiment 3: Assay Using Sensor Surface of the Invention

The chip from Experiment 1 was assembled with plastic carrier and hood. The chip was docked in a Biacore® 8K according to instruction in control software. The carboxyl groups on SAM were activated in the instrument with a mixture of 200 mM EDC and 50 mM NHS in water for 30 seconds.

30 µg/ml Mouse anti-$\beta_2\mu$ in 10 mM sodium acetate pH 5 was injected over the activated chip surface for 7 minutes. The chip surface (not reacted succinimide esters) was deactivated with 1 M Ethanolamine pH 8.5 for 5 minutes. Different concentration of $\beta_2\mu$ (1, 2, 4, 8, 16 nM) in running buffer were injected over the immobilized surface and a reference spot/surface without ligand. Running buffer was HBS-P+. $\beta_2\mu$ binding kinetics to Mouse anti-$\beta_2\mu$ was possible to determine. Fit to a one to one binding model was applied.

Figure 4:
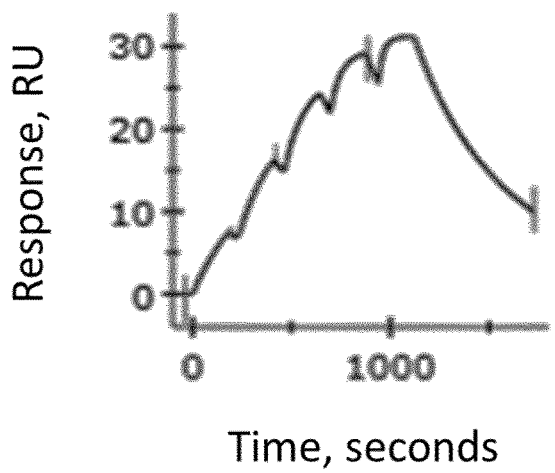
FIG. 4 is a sensorgram from a kinetic characterization assay with immobilized ligand (30 s activation) on PEG surface synthesized according to FIG. 1/Experiment 3.

For this Example reference is made to FIG. 4 which shows the reference subtracted sensorgram. Through the Biacore® 8K evaluation software the association constant (ka), dissociation constant (kd) and the affinity constant (KD) were calculated. The result was in accordance to previously established available result.

The invention claimed is:

1. A method for preparing a sensor surface for a surface plasmon resonance (SPR) instrument, comprising forming a self assembled monolayer (SAM) on a surface by reacting said surface with one or more thiol C10-C30 alkane reagent(s) having at least one type of functional groups, wherein one or more protein resistant compound(s) is/are coupled to a first fraction of said functional group(s), wherein the one or more protein resistant compound(s) comprise polyethylene glycol (PEG) or a derivative thereof; and wherein one or more capturing molecule(s) is/are coupled directly or via a linker which is not said protein resistant compound(s) to a second fraction of said functional group(s) on said surface, wherein no capturing molecule(s) is/are coupled to the protein resistant compound(s), wherein the second fraction of said functional group(s) comprises a portion of the at least one type of functional groups not coupled to the one or more protein resistant compound(s) after the coupling of the protein resistant compound(s) via the first fraction of the functional group(s), and wherein the first and second fraction of said functional group(s) are of the same or different type.

2. The method according to claim 1, wherein the surface is a metal plated surface.

3. The method according to claim 1, wherein the functional group of the one or more C10-C30 thiol alkane reagent(s) is one or more of a carboxyl, a hydroxyl, an amino, an aldehyde, an epoxy, a vinyl, a carbonyl or thiol group.

4. The method according to claim 1, wherein the C10-C30 thiol alkane reagent is MHA (mercapto hexadecanoic acid) or derivatives thereof.

5. The method according to claim 1, wherein the one or more protein resistant compound(s) have a molecular weight (mw)<20000.

6. The method according to claim 1, wherein the polyethylene glycol (PEG) has a mw of 100-20000.

7. The method according to claim 1, wherein the second fraction of the functional group(s) are activated with an activation reagent before coupling of the one or more capturing molecule(s) and an amount of the one or more capturing molecule(s) coupled to the second fraction of the functional group(s) is inversely proportional to a length of activation time; and wherein the activation reagent is selected from N-Ethyl-N'-(3-Dimethylaminopropyl) Carbodiimide/N-Hydroxy-succinimide (EDC/NHS), epichlorhydrine or bifunctional reagents.

8. A method for running an SPR assay using a sensor surface produced according to claim 1, comprising adding an analyte; interacting the analyte with the capturing molecule on the sensor surface and performing a kinetic assay and/or concentration assay.

9. A sensor surface produced according to claim 1, comprising a substrate with a self assembled monolayer (SAM) provided with functional group(s) available on said SAM, wherein the SAM is a thiol-alkane C10-C30, wherein a protein resistant compound is coupled to a first fraction of the functional group(s), wherein the protein resistant compound is polyethylene glycol (PEG) or a derivative thereof, and wherein a capturing molecule is coupled to a second fraction of the functional group(s) on the surface, and wherein no capturing molecule is coupled to the protein resistant compound, wherein the second fraction of said functional group(s) comprises a portion of said functional group(s) not coupled to the protein resistant compound after the coupling of the protein resistant compound via the first fraction of the functional group(s), and wherein the first and second fraction of said functional group(s) are of the same or different type.

10. The sensor surface according to claim 9, wherein the protein resistant compound and the capturing molecule are coupled to the same type of functional group.

11. The sensor surface according to claim 9, wherein the protein resistant compound and the capturing molecule are coupled to different types of functional groups.

12. The sensor surface according to claim 9, wherein the surface is a metal plated surface and the thiol-alkane C10-C30 is MHA-SAM.

13. The sensor surface according to claim 9, wherein the protein resistant compound is PEG mw 5000 in a concentration of 0.5-5 mM.

* * * * *